United States Patent [19]

Arena

[11] 4,367,355
[45] Jan. 4, 1983

[54] HYDROGENATION USING CHITIN AND CHITOSAN BASED IMMOBILIZED METAL CATALYSTS

[75] Inventor: Blaise J. Arena, Des Plaines, Ill.

[73] Assignee: UOP Inc., Des Plaines, Ill.

[21] Appl. No.: 237,030

[22] Filed: Feb. 23, 1981

Related U.S. Application Data

[63] Continuation-in-part of Ser. No. 83,926, Oct. 11, 1979, Pat. No. 4,274,980.

[51] Int. Cl.³ .......................... C07C 5/02; C07C 5/03; C07C 5/08
[52] U.S. Cl. .................................... 585/269; 585/276; 585/277
[58] Field of Search ....................... 585/269, 276, 277

[56] References Cited

U.S. PATENT DOCUMENTS 4,274,980 6/1981 Arena .................................. 585/276

Primary Examiner—Delbert E. Gantz
Assistant Examiner—Helane E. Maull
Attorney, Agent, or Firm—James R. Hoatson, Jr.; Eugene I. Snyder; William H. Page, II

[57] ABSTRACT

Group VIII metals immobilized on an aminated polysaccharide in a highly dispersed state are active catalysts in the hydrogenation of unsaturated organic materials. Chitin and chitosan are preferred supports, with platinum and palladium among the more active Group VIII metals in hydrogenation.

5 Claims, No Drawings

HYDROGENATION USING CHITIN AND CHITOSAN BASED IMMOBILIZED METAL CATALYSTS

CROSS-REFERENCE TO RELATED APPLICATION

This application is a continuation-in-part of my copending application Ser. No. 83,926, filed Oct. 11, 1979, now U.S. Pat. No. 4,274,980 all of which is incorporated herein by reference.

BACKGROUND OF THE INVENTION

Metals are used as catalysts in a diversity of chemical processes. Ideally, it is desired to have such metals in as finely dispersed a state as possible so as to maximize catalytic activity. When metals are used in their most highly dispersed state, a batch-type process is often employed. Removal of the catalyst in subsequent processing is disadvantageous because of attending loss of metal and the necessity for a costly separation stage. Therefore, metals commonly are deposited on an appropriate supporting medium in a more discrete fashion, for example, as extrusions, tablets, pellets, etc. Utilization of the metal in such a form permits continuous processes, but it is found that the metal is not in such a finely dispersed state as is otherwise possible. Furthermore, transport phenomena become important because much of the metal is in the interior of the supporting medium and not on its surface.

A discovery of this invention is that chitin and chitosan are desirable supports for zerovalent metals which are active catalysts in hydrogenation of unsaturated organic materials. In particular, zerovalent metals can be supported on chitin and chitosan in a highly dispersed state to afford active catalysts which, when the metal is one of the Group VIII metals, are effective in hydrogenation of a variety of unsaturated organic materials, including alkenes, alkynes, and aromatic compounds. The process of hydrogenation which is the invention disclosed herein is a noteworthy addition to the arsenal of hydrogenation methods, the latter occupying a central position in commercial chemical processes.

SUMMARY OF THE INVENTION

An object of this invention is to provide a method of hydrogenating unsaturated organic materials. An embodiment is the process comprising contacting a catalyst composition consisting essentially of a Group VIII metal on an aminated polysaccharide support with a feedstock containing unsaturated organic material in the presence of hydrogen so as to effect hydrogenation of the unsaturated material. In a more specific embodiment, the aminated polysaccharide is chitin or chitosan. In a still more specific embodiment, the metal is palladium or platinum.

DESCRIPTION OF THE INVENTION

Chitin is a polysaccharide available in large quantities from the shells of crustaceans, a waste product of the fishing industry, and is the polymer of N-acetylglucosamine,

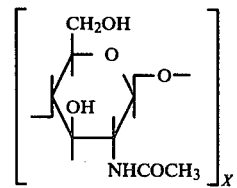

Deacetylation of chitin leads to chitosan. Both chitin and chitosan have good mechanical strength, and liquids show good flow properties in a bed or column of these polysaccharides. Furthermore, both chitin and chitosan complex or bind with metals. Chelation of a single metal ion by several $NH_2$ or $-NHCOCH_3$ groups effectively isolates each metal ion from its neighbors. If such isolation is maintained, wholly or in large part, during subsequent reduction of the metal to its zerovalent state, then such metals may be found in a highly dispersed state largely on the surface of the polysaccharide, thereby being relatively available to flowing liquids. Therefore, chitin and chitosan should be useful as metal supports in catalytic processes. Indeed, this invention demonstrates the veracity of such an hypothesis.

The chitin or chitosan used in this invention may be in the form of a powder, flakes, or may even be granular in form. Both chitin and chitosan readily absorb metals from aqueous solutions. Since chitin normally is about 85% acetylated, it is to be expected that chitin has a lower capacity to absorb metal ions than does chitosan. Nonetheless, chitin does show appreciable absorptive capability toward some metals.

Although a diversity of metals can be absorbed by chitin or chitosan, Group VIII metals are of particular importance and interest because of their catalytic properties and usage in a process of hydrogenation of unsaturated organic material. Within this group iron, cobalt, nickel, ruthenium, rhodium, palladium and platinum are of prime interest, although osmium and iridium also may be used, but not necessarily with equivalent results. The metals are absorbed from a solution of their salts, where the metals exhibit a valence state from about 1 to about 4, depending upon the chemical characteristics of the individual metal. The absorbed metal may then be reduced, wholly or in part, to its zerovalent state. A major portion, by which is meant 51% or more, of the metal will be in the zerovalent state and usually the metal will be substantially entirely in its zerovalent state. Frequently the metal will be prereduced, that is, the metal dispersed in an ionic state on the aminated polysaccharide will be reduced, wholly or in part, to its zerovalent state prior to its use as a hydrogenation catalyst. However, under some circumstances the catalyst may be formed in situ, by which is meant that the metal dispersed in an ionic state on an aminated polysaccharide is reduced to the active hydrogenation catalyst, where the metal is in the zerovalent state, while in contact with the feedstock containing unsaturated organic material under hydrogenation conditions.

It is to be understood that several metals in varying ratios may be deposited either concurrently or serially to give a mixed-metal impregnated chitin or chitosan. Similarly, the impregnated metal may be reduced only partly to give a polysaccharide bearing a mixture of oxidation states of the metal or metals deposited thereon, with the major portion of total metals being in the zerovalent state.

Absorption of the metal is effected simply by contacting chitin or chitosan in a suitable physical form with an aqueous solution of the metal salt, preferably with mixing to ensure good contact. The conditions of contacting are not critical so long as the chitin or chitosan is not degraded, nor their absorptive capacity appreciably impaired, and the salt of, or acid containing, the metal remains in solution. To avoid degradation of chitin or chitosan, concentrated mineral acids (above about 1 molar) and caustic (above about 20%) at temperatures above about 100° C. should be avoided. After mixing, the metal impregnated polysaccharide is separated and washed to remove loosely adhering excess metal.

The metal is converted to its zerovalent state by treatment with a reducing agent, for example, a reducing sugar, such as glucose, or formaldehyde. Frequently the reducing agent may be hydrogen. Where appropriate the reducing agent is removed by suitable means before the catalyst is employed for its intended use. For example, where glucose or formaldehyde is used the metal impregnated chitin or chitosan may be washed with water to remove the reducing agent. In contrast, where hydrogen is used as the reducing agent, no further treatment is necessary after treatment with hydrogen, and reduction often can be done advantageously in situ. The concentration of metals on chitin or chitosan may range from about 0.01 to about 10% by weight depending upon its intended use, the metal employed, and the salt used in the preparation of the supported catalyst system.

The catalysts described above may be advantageously employed in a process for the hydrogenation of unsaturated organic materials, which process comprises contacting said catalyst with a feedstock containing unsaturated organic material in the presence of hydrogen so as to effect hydrogenation of said unsaturated organic material. By unsaturated organic material is meant organic compounds characterized by the presence of reducible, or hydrogenatable, functional groups such as the carbon-carbon double bond, carbon-carbon triple bond, carbon-oxygen double bond, carbon-nitrogen double bond, carbon-nitrogen triple bond, nitrogen-oxygen double bond, and nitrogen-nitrogen double bond. Thus, the process of this invention has broad application to a wide range of unsaturated materials. Among such materials are included alkenes, alkynes, aromatic compounds, aldehydes, ketones, imines, nitriles, nitroso compounds, nitro compounds and azo compounds.

Solely for the purpose of illustration and exemplification of this invention, the process of this invention may be described in greater detail with regard to alkenes. Hydrogenation may be effected of terminal alkenes, commonly known as alpha olefins, and non-terminal alkenes, commonly known as internal olefins. Terminal alkenes may be relatively short chain materials, as illustrated by 1-butene, 1-pentene, 1-hexene, 1-heptene, 1-octene, 2-methylpentene, 2-ethylpentene, and so on. The terminal alkenes may also be intermediate chain materials, as well as longer chain materials as represented by 1-eicosene, 1-heneicosene, 1-docosene, 1-tricosene, 1-pentacosene, 1-triacontene, 4-butyl-1-eicosene, 2-octyl-1-hexadecene, and so on.

Internal alkenes may be of similar chain length, encompassing short, intermediate, and long chain unsaturated compounds. Internal alkenes may be disubstituted alkenes, or alpha, beta-disubstituted olefins, as exemplified by compounds such as 2-butene, 2-octene, 3-octene, 4-octene, 7-octadecene, and so on. Internal alkenes also may be tri- and even tetrasubstituted alkenes. By "trisubstituted alkenes" is meant alkenes where the carbon atoms of the double bond bear only one hydrogen; by "tetrasubstituted alkenes" is meant alkenes where the carbon atoms of the double bond bear no hydrogen atoms. Examples of trisubstituted alkenes which illustrate the group are 3-methyl-2-pentene, 3-ethyl-3-nonene, 6-propyl-5-tetradecene, and 11-pentyl-10-heneicosene. Examples of tetrasubstituted alkenes which illustrate the group are 2,3-dimethyl-2-butene, 5-ethyl-6-methyl-5-undecene, and 9-cyclohexyl-8-methyl-8-octadecene. As a group the tetrasubstituted alkenes are often difficultly reducible, a characteristic which they retain in the process of this invention.

It is to be understood that alkenes, as hydrocarbons which bear a reducible carbon-carbon double bond, may be replaced by other materials which also bear the carbon-carbon double bond but additionally have functional groups ordinarily nonreducible in the process of this invention. Thus, functional groups which are inert and may be borne by the unsaturated organic materials in this invention include hydroxyl (alcohols), carboxyl (carboxylic acids), alkoxycarbonyl (carboxylic esters), alkoxy (esters), halogen (halides), sulfonyloxyl (sulfonic acids), carbosulfonyloxy (sulfonic acid esters), amino (primary, secondary, and tertiary amines), carboxamide (carboxylic acid amides), and sulfonamide (sulfonic acid amides).

The process of this invention may be carried out in either a batch or continuous mode. For example, if performed in a batch mode, the feedstock, containing unsaturated organic material is contacted with an effective amount of the catalyst and hydrogen under reaction conditions. The amount of catalyst used depends, inter alia, on the unsaturated organic material to be hydrogenated, the Group VIII metal used, the temperature, hydrogen pressure, and degree of mixing. For example, when the Group VIII metal is platinum, the catalyst is present in an amount to give from about 0.0001 to about 0.1% of platinum by weight based on the unsaturated organic material. When nickel is used, the metal is present in from about 0.01 to about 1% by weight on the same basis.

Hydrogen pressure may range from about atmospheric to several hundreds of atmospheres. Limitations in pressure arise from limitations of equipment rather than being an inherent property of the catalyst. In the usual case, hydrogenation is conducted at pressures from about 5 to about 1000 psig.

On the other hand, the nature of the catalyst support does impose a temperature limitation because of degradation of aminated polysaccharides at a temperature above about 275° C. This latter temperature places an upper limit on the temperature at which the process may be performed, and since degradation occurs, albeit more slowly, even below 275° C., it is preferred that the temperature remain less than about 250° C., and a limit of about 225° C. is even more preferred. Where reaction times are prolonged or where the catalyst is held at an elevated temperature for prolonged periods of time, as for example in continuous hydrogenation, it is desirable that the temperature does not exceed about 200° C. Although some hydrogenations may be performed at a temperature as low as about 50° C., generally the process is carried out at a temperature of at least about 80° C.

The examples below merely serve to illustrate the invention described herein and are not intended to be construed as limitations thereof.

EXAMPLE 1

Palladium chloride, 0.4 g, dissolved in 20 ml of 2 M hydrochloric acid was stirred with 1.0 g of coarse chitosan flakes for ten minutes. The solid was then removed by filtration and washed with 100 ml of deionized water. The washed material was suspended in 10 ml of deionized water to which was added 20 ml of 2% potassium hydroxide and 20 ml formaldehyde. This suspension was stirred at 50° C. for 15 minutes, after which the palladium impregnated chitosan was filtered, washed with 100 ml of deionized water, and dried for 16 hours at 50° C. under vacuum. The product upon analysis contained 5.0% palladium.

EXAMPLE 2

A solution of 0.8 g palladium chloride in 20 ml of 2 M hydrochloric acid was stirred with 2.0 g of chitin powder for 30 minutes. The solid removed by filtration, was washed with 200 ml of deionized water, then resuspended in 20 ml of 5% potassium hydroxide containing 2.0 g glucose. This suspension was stirred at 80° C. for three hours, after which solid was removed by filtration, washed with 200 ml of deionized water, and dried for 16 hours at 50° C. under vacuum. The material so obtained contained 1.75% palladium.

EXAMPLE 3

A suspension of 6.4 g chitin powder in 20 ml of 0.18 M chloroplatinic acid and 20 ml of deionized water was stirred for 45 minutes. After removal by filtration, the solid was washed with 150 ml of deionized water, thereafter resuspended in 50 ml of 5% potassium hydroxide containing 2.0 g glucose, and the suspension was heated at 90° C. for three hours with stirring. Removing the solid by filtration, washing with 200 ml of deionized water and drying for 16 hours at 50° C. under vacuum gave a platinum impregnated chitin containing 0.25% platinum.

EXAMPLE 4

A mixture of 100 ml of 1-heptene and 2.0 g of catalyst as prepared in Example 3 was placed in a 250 cc stainless steel autoclave. The reactor was pressurized with hydrogen to 700 psig and maintained at 175° C. for 1.5 hours. Analysis of the product by gas liquid partition chromotography showed 36.5% 1-heptene, 49.6% n-heptane, 1.1% of trans- and cis-3-heptene, 5.0% trans-2-heptene, 2.8% cis-2-heptene, and 5% of unidentified material.

Thus the catalyst showed appreciable activity in hydrogenation, and also demonstrated an ability to isomerize terminal olefins.

What is claimed is:

1. A process for the hydrogenation of unsaturated organic materials consisting of unsaturated hydrocarbons comprising contacting an effective amount of a catalyst, said catalyst containing a zerovalent Group VIII metal immobilized in a highly dispersed state on an aminated polysaccharide as a support, with a feedstock containing said unsaturated organic material in the presence of hydrogen so as to effect the hydrogenation of said unsaturated organic material.

2. The process of claim 1 wherein the aminated polysaccharide is chitin or chitosan.

3. The process of claim 1 wherein the Group VIII metal is selected from the group consisting of ruthenium, rhodium, palladium, platinum, cobalt and nickel.

4. The process of claim 3 where the metal is palladium or platinum.

5. The process of claim 1 where the unsaturated organic material is characterized by the presence of at least one reducible group selected from the group consisting of the carbon-carbon double bond and carbon-carbon triple bond.

* * * * *